US010034888B2

(12) United States Patent
Gilbert et al.

(10) Patent No.: US 10,034,888 B2
(45) Date of Patent: *Jul. 31, 2018

(54) METHOD FOR MAKING BISMUTH CONTAINING LIQUID PHARMACEUTICAL SUSPENSIONS

(71) Applicant: The Procter & Gamble Company, Cincinnati, OH (US)

(72) Inventors: Steven Ray Gilbert, Fairfield, OH (US); Edward Paul Fitch, V, Cincinnati, OH (US); Derrick Ho, Maineville, OH (US); Daniel Jerome White, Jr., West Chester, OH (US); Adam Michael Tunis, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,470

(22) Filed: Oct. 10, 2016

(65) Prior Publication Data

US 2017/0027964 A1 Feb. 2, 2017

Related U.S. Application Data

(63) Continuation of application No. 14/698,962, filed on Apr. 29, 2015, now Pat. No. 9,486,436.

(60) Provisional application No. 61/985,653, filed on Apr. 29, 2014.

(51) Int. Cl.
| | | |
|---|---|---|
| *A61K 31/36* | (2006.01) | |
| *A61K 31/621* | (2006.01) | |
| *A61K 31/29* | (2006.01) | |
| *A61K 9/10* | (2006.01) | |
| *A61K 47/02* | (2006.01) | |
| *A61K 9/00* | (2006.01) | |
| *A61K 47/36* | (2006.01) | |
| *A61K 47/38* | (2006.01) | |
| *A61J 3/00* | (2006.01) | |

(52) U.S. Cl.
CPC ............ *A61K 31/621* (2013.01); *A61J 3/00* (2013.01); *A61K 9/0095* (2013.01); *A61K 9/10* (2013.01); *A61K 31/29* (2013.01); *A61K 47/02* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,801,454 A * | 1/1989 | Coveney | A61K 33/245 424/653 |
| 5,013,560 A | 5/1991 | Stentz et al. | |
| 6,482,865 B1 | 11/2002 | Palafox, Sr. | |
| 6,712,496 B2 * | 3/2004 | Kressin | B01F 13/06 366/139 |
| 7,135,197 B2 | 11/2006 | Pena et al. | |
| 8,394,752 B2 | 3/2013 | Erbezci et al. | |
| 2005/0089577 A1 | 4/2005 | Yokoyama et al. | |
| 2008/0008814 A1* | 1/2008 | Jackson | A23C 9/1542 426/590 |
| 2008/0193523 A1* | 8/2008 | Heim | A61K 9/4858 424/463 |
| 2008/0227892 A1 | 9/2008 | Van Der Wielen et al. | |
| 2009/0069207 A1 | 3/2009 | Panandiker et al. | |

FOREIGN PATENT DOCUMENTS

| | | |
|---|---|---|
| EP | 1 488 812 A1 | 12/2004 |
| GB | 1269987 | 4/1972 |
| WO | WO 2000/10527 | 3/2000 |
| WO | WO 2003/066022 A2 | 8/2003 |

OTHER PUBLICATIONS

Corcoran, Journal of the American Pharmaceutical Association 1941, 220-221.*
International Search Report and Written Opinion for 13318M—PCT/US2015/028215—dated Jul. 13, 2015.
Corcoran, Journal of the American Pharmaceutical Association 1941, pp. 220-221.
All Office Actions for U.S. Appl. No. 14/698,962, filed Apr. 29, 2015.

* cited by examiner

*Primary Examiner* — Jeffrey S Lundgren
*Assistant Examiner* — Michael J Schmitt
(74) *Attorney, Agent, or Firm* — Amanda Herman; Alexandra S. Anoff

(57) ABSTRACT

A method of producing a liquid pharmaceutical suspension by mixing magnesium aluminum silicate, gellan gum, bismuth subsalicylate, and methyl cellulose.

20 Claims, 2 Drawing Sheets

METHOD FOR MAKING BISMUTH CONTAINING LIQUID PHARMACEUTICAL SUSPENSIONS

FIELD OF THE INVENTION

The present invention relates to methods of making a suspension, particularly a bismuth-containing pharmaceutical suspension.

BACKGROUND OF THE INVENTION

Bismuth is a common active in over-the-counter liquid pharmaceutical formulations. Pharmaceutical formulations containing bismuth are often sold as suspensions (e.g. Pepto-Bismol®, distributed by Procter & Gamble®), which can be used to treat gastrointestinal symptoms including nausea, heartburn, indigestion, upset stomach, and diarrhea.

It can be difficult to make suspensions, particularly suspensions that are consumer desirable and contain containing insoluble pharmaceutical salts such as bismuth subsalicylate. First, making a suspension with the correct rheology can be difficult. If the rheology is insufficient then the suspension can quickly separate into phases. Furthermore, air bubbles and/or foam can also form during processing, which can also slow batch time, increase waste, and produce a less desirable suspension. Air bubbles can be removed by degassing the suspension over a significant period of time prior to packaging and foam can be removed and discarded from the suspension and also must be cleaned out of the system.

As such, there remains a need for a process for making stable suspensions containing bismuth that reduces batch time and reduces waste by reducing the amount of air that gets mixed into the formulation, while making a suspension that is desirable to consumers.

SUMMARY OF THE INVENTION

A method of making a liquid pharmaceutical suspension comprising: (a) mixing magnesium aluminum silicate with an aqueous media to form a first mixture; (b) mixing gellan gum with the first mixture to form a second mixture; (c) mixing a bismuth slurry with the second mixture to form a third mixture; (d) mixing methyl cellulose with the third mixture to form a liquid pharmaceutical suspension.

A method of making a suspension comprising: (a) adding a suspension system component comprising a solid powder to an aqueous media to form a first mixture utilizing a hopper for containing the suspension system component, the hopper having a hopper inlet for receiving the suspension system component and a throat for distributing the suspension system component the throat comprises a throat inlet for receiving solids from the hopper and a throat outlet for discharging solids from the throat wherein a vertically oriented auger disposed in the throat wherein the throat outlet is connected to a disperser at a connection and wherein the connection is substantially free of air; and (b) adding an internal phase to form a suspension.

DETAILED DESCRIPTION OF THE INVENTION

Figure 1:
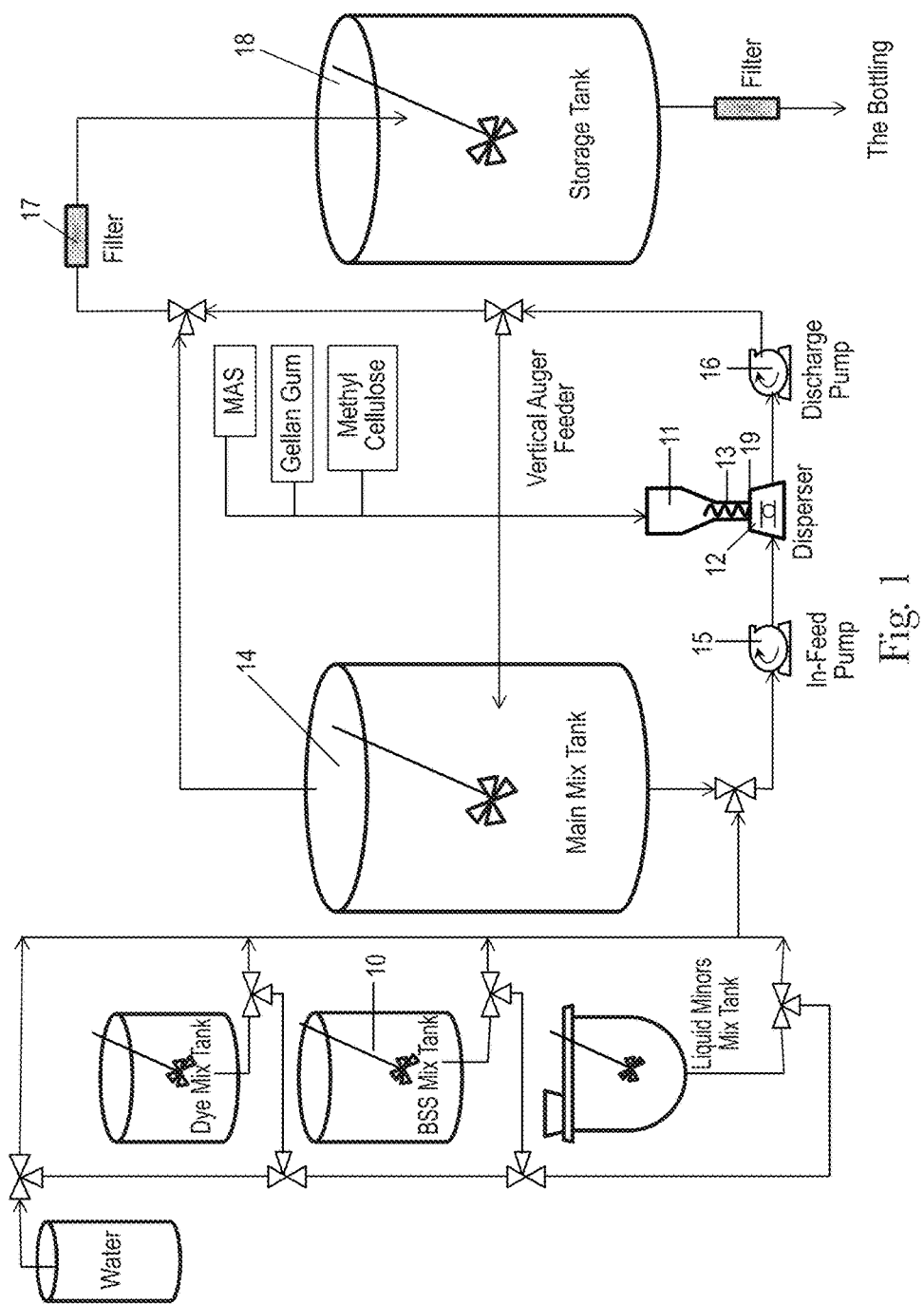
FIG. 1 is a process flow chart showing an embodiment of the invention.

One aspect of the present invention involves combining suspension system components, which can include magnesium aluminum silicate (MAS, commercially available from Vanderbilt Minerals, Norwalk, Conn., USA), gellan gum (commercially available from CP Kelco, San Diego, Calif., USA), and methyl cellulose (commercially available from Ashland Chemical, Covington, Ky., USA) in a specific way, in order to obtain a liquid formulation with the desired rheology. This can also reduce the formation of agglomerates during processing. In some examples adding the gellan gum after the MAS can lead to a product that is more desirable consumers. Adding the methyl cellulose late in the process, can also help to decrease the amount of air that is in the system.

The suspensions system components can be solid powders that can be placed into a hopper. The hopper can have a hopper inlet for receiving solids powders, such as the suspension system components, and a throat that is adapted to discharging or otherwise distributing the suspension system components there from. The throat can have an auger that meters the suspension system components and can be situated inside the throat. The throat can be connected to a disperser at a connection and the disperser can draw in and apply shear that can aid in incorporating the suspension system components into the liquid phase of the formulation.

It can also be important to limit the amount of air that enters the system resulting in air bubbles and foam. Excessive foam needs to be cleaned, removed, or drained from the system and discarded, increasing batch time and waste. Foam can also become lodged in the processing and venting systems and resulting in the system needing to be cleaned more frequently. Air bubbles get trapped in the formulation and the formulation needs to be stored in order to deaerate product before bottling. In an example, this problem can be significantly lessened if the solids metering device described herein is used which incorporates air resistance in the storage and metering portions of the delivery system and if the connection between the throat of the hopper and the disperser is substantially air tight and if the components are added at in a certain order.

As used herein, the word "agglomerate" refers to collections of undispersed accumulations of solids, semi-solids, or gels in the liquid formulations. Agglomerates can include gel balls and fish-eyes, which are accumulations that are wetted throughout, and accumulations where the outside is wet and the inside is dry and powdery. The agglomerates can be any shape. In an example, an agglomerate can be approximately spherical. In another example, the agglomerate can be round and in another example the agglomerate can be long and thin, like a spaghetti noodle.

As used herein, the word "or" when used as a connector of two or more elements is meant to include the elements individually and in combination; for example X or Y, means X or Y or both.

As used herein, the word "water" refers to USP (United States Pharmacopeia) purified water, unless otherwise noted.

An illustrative processing diagram of the instant invention is depicted in FIG. 1. First, a slurry can be made with an internal phase. An internal phase can be the solid portion of the suspension that is dispersed throughout the liquid external phase. In an example, the internal phase can be bismuth subsalicylate (BSS) and a bismuth slurry can be made by combining powdered BSS with water in BSS mix tank 10. The bismuth slurry is mixed until a uniform slurry is formed and stored in BSS mix tank 10 until it is ready to be incorporated into the main mixture. A uniform mixture is a type of mixture in which the composition is uniform and every part of the solution or suspension can have substantially the same properties. The bismuth slurry can contain an appropriate amount of bismuth. If the bismuth slurry contains too much bismuth, for instance greater than about 60% bismuth, then the bismuth will not suspend in water and the slurry may be too thick, for example the slurry can resemble sludge. If the bismuth slurry contains too little bismuth, for instance less than about 2%, there will be too much water and it will not be possible to make the product at the desired specifications. In an example, the bismuth slurry contains from about 3.5% to about 60% bismuth, in another example from about 5% to about 40% bismuth, in another example from about 7% to about 30% bismuth, and in another example from about 8% to about 15% bismuth. In an example, the bismuth slurry can contain about 10% bismuth.

The particle size of the bismuth can be important in making a suspension that can be easily be resuspended when a consumer shakes the bottle. In some examples, if the bismuth particles are too large, for instance if the average particle diameter is about 100 μm or larger, it can be difficult to resuspend the bismuth and it can settle too quickly. In another example, if the average particle diameter is smaller, for instance if the average particle diameter is about 3 μm, the suspension can resuspend more easily. In an example the bismuth particles can have an average diameter from about 0.5 μm to about 100 μm, in another example from about 1 μm to about 75 μm, in another example from about 2 μm to about 50 μm, in another example from about 3 μm to about 25 μm, and in another example from about 3 μm to about 10 μm.

In an example, the final formulation can have about 17.5 mg/mL BSS and in another example, the final formulation can have about 35 mg/mL BSS.

The next step is to make the main mix, which can be the final mixture for the formulation. The main mix can be made at ambient temperature. In some examples the initial and long term rheology of the formulation can be improved when the process is performed at ambient temperature. Processing at ambient temperature can save cost and time, as the components do not have to be heated and cooled.

In an example, the process is performed at ambient temperature, which can fluctuate between about 15° C. and about 27° C. In another example, the process can be performed between 17° C. to about 80° C., in another example from about 23° C. to about 70° C., in another example from about 25° C. to about 60° C., in another example from about 28° C. to about 50° C., and in another example from about 30° C. to about 40° C. In another example, the process can be performed between about 17° C. to about 27° C.

Figure 2A:
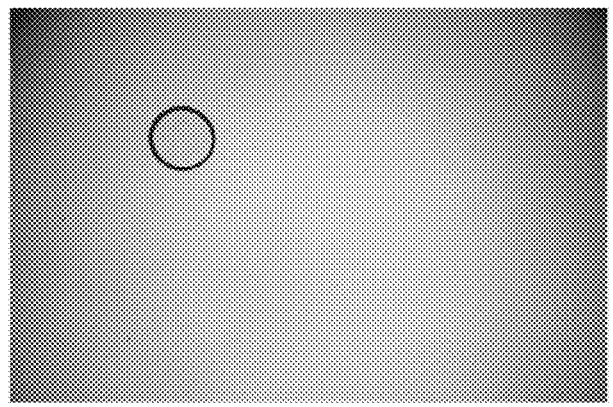
FIG. 2A is a digital photograph of gellan gum in water using a light microscope and a 10× stage, where the gellan gum was added to water at 70° C. and cooled.

In certain examples, when the process is performed at room temperature, the gellan gum can form aggregates of small particles. While not wishing to be bound by theory, when the gellan gum is added at an elevated temperature, such as 70° C., and then cooled, as commonly recommended, the gellan gum can spread significantly. FIG. 2A shows digital photograph using a light microscope and an 10× stage of a solution containing 0.0545% (w/w) gellan gum where the gellan gum was added to water that was 70° C. and then the solution was cooled at ambient conditions until the solution reached ambient temperature. The solution appears substantially clear, with the exception of an air bubble on the left side, since the gellan gum has not formed discernible aggregates, the gellan gum cannot be easily seen at this microscopy.

Figure 2B:
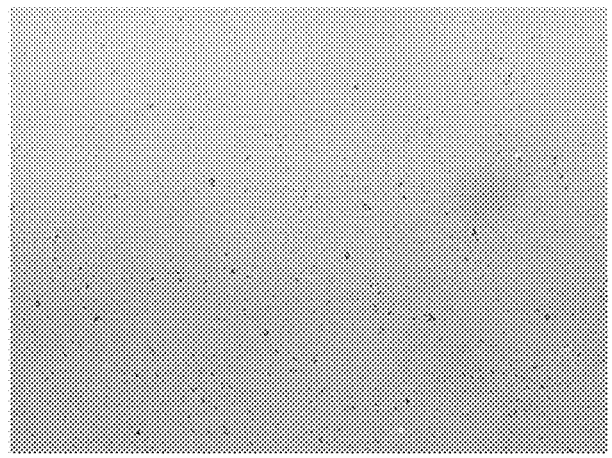
FIG. 2B is a digital photograph of gellan gum in water using a light microscope and an 10× stage, where the gellan gum was added to water at ambient temperature.
Figure 2C:
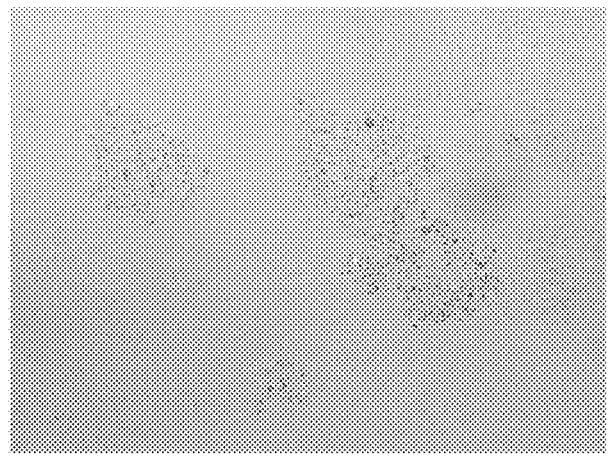
FIG. 2C is a digital photograph of gellan gum in water using a light microscope and an 10× stage, where the gellan gum was added to a formulation of water and magnesium aluminum silicate at ambient temperature.

In some examples, gellan gum can form aggregates when added to liquid at room temperature. FIGS. 2B and 2C are digital photographs of a solution containing 0.0545% (w/w) gellan gum using a light microscope and a 10× stage. FIG. 2B shows gellan gum added to water at ambient temperature and FIG. 2C shows gellan gum added a solution containing water and MAS, which is an ionic formulation, at ambient temperature. The gellan gum particles in FIG. 2C formed larger aggregates than the gellan gum particles in FIG. 2B, which formed smaller aggregates.

In some examples, adding the MAS before the gellan gum can also increase the initial rheology of the formulation. While not wishing to be bound by theory, it is believed that the ions in the MAS can prevent the gellan gum from fully dispersing in the formulation.

In an example, the gellan gum aggregates can be out-of-round. The gellan gum aggregates can have a mean length of from about 50 μm to about 2000 μm, in another example from about 100 μm to about 1000 μm, in and in another example from about 200 μm to about 400 μm. The mean length can be determined by the Mean Length Test Method, described hereafter. In another example, a discernible amount of gellan gum aggregates are may be found when the formulation or a formulation containing gellan gum and water is strained through a 10 mesh (2000 μm sieve size).

The main mix can be made by adding the suspension system components one at a time into hopper 11 (Model A-100, commercially available from AMS®, Inc., Honey Brook, Pa., USA). The suspension system components can be solid powders and can include MAS, gellan gum, and methyl cellulose. In some examples, changing the order of addition of the formulation including the suspension system components and the bismuth can significantly alter the initial low shear viscosity (LSV) and can also minimize the incorporation of air.

In an example, the suspension system components are added in the following order: MAS, gellan gum, and then methyl cellulose. In another example, the bismuth slurry can be added after the gellan gum, in another example the bismuth slurry can be added after the MAS, and in another example the bismuth slurry can be added before the methyl cellulose.

In another example, the suspension system components can be added in the following order: MAS, methyl cellulose, and then gellan gum. In another example, the bismuth slurry can be added after the gellan gum, in another example the bismuth slurry can be added after the MAS, and in another example the bismuth slurry can be added before the methyl cellulose.

In another example, the suspension system components can be added in the following order: methyl cellulose, MAS, and then gellan gum. In another example, the bismuth slurry can be added after the gellan gum, in another example the bismuth slurry can be added after the MAS, and in another example the bismuth slurry can be added before the methyl cellulose.

In another example, the suspension system components can be added in the following order: methyl cellulose, gellan gum, and then MAS. In another example, the bismuth slurry can be added after the gellan gum, in another example the bismuth slurry can be added after the MAS, and in another example the bismuth slurry can be added before the methyl cellulose.

In another example, the suspension system components (methyl cellulose, gellan gum, and MAS) can be added concurrently.

Generally when making a suspension, the suspending system, can include MAS, gellan gum, and methyl cellulose that are added before adding the internal phase, which can be bismuth. However, in some examples adding the methyl cellulose as one of the final components can minimize the incorporation of air.

The hopper can have a sweeper arm that mixes the contents of the hopper and prevents them from clumping together. The hopper can be made out of any suitable low friction material including, but not limited to, metals including stainless steel, polymeric materials, and combinations thereof. In an example, the inside surfaces of the hopper can be polished by any known method including, but not limited to, electropolishing, mechanical grinding, and combinations thereof.

Hopper 11 can have throat 19 for discharging or otherwise distributing the solids therefrom. The throat can be connected to disperser 12 (such as the Quadro Ytron® ZC1 high speed disperser, available from Quadro Engineering, Ontario, Canada) and the connection can be substantially air tight.

In an example, the suspension can have a density from about 0.6 g/cc to about 1.25 g/cc according to the Density Test Method described herein when a sample is removed after the batch is completed, immediately before it is transferred to the storage tank or filtered, in another example from about 0.7 g/cc to about 1.2 g/cc, in another example from about 0.8 g/cc to about 1.1 g/cc, in another example from about 0.9 g/cc to about 1.05 g/cc, in another example from about 0.95 g/cc to about 1.03 g/cc, and in another example from about 0.97 g/cc to about 1.02 g/cc. In another example, the density is greater than about 0.6 g/cc according to the Density Test Method described herein, when a sample is removed immediately after the batch is completed, before it is transferred to the storage tank or filtered, in another example greater than about 0.7 g/cc, in another example greater than about 0.8 g/cc, in another example greater than 0.9 g/cc, and in another example greater than 1.0 g/cc. In another example, the formulation can have a density from about 0.7 g/cc to about 1.75 g/cc according to the Density Test Method described herein, when a sample is removed immediately prior to bottling, in another example from about 0.8 g/cc to about 1.5 g/cc, in another example from about 0.9 g/cc to about 1.25 g/cc, in another example from about 0.95 g/cc to about 1.10 g/cc and in another example from about 1.00 g/cc to about 1.04 g/cc.

In another example, backpressure can be applied to the system between disperser 12 and discharge pump 16. One way to increase the backpressure to the disperser can be to adjust the speed of the discharge pump and slow the liquid flowrate. In an example, the backpressure is from about 3 psig to about 30 psig, in another example from about 15 psig to about 25 psig, in another example from about 10 psig to about 20 psig, and in another about 5 psig to about 15 psig. The backpressure can be used alone or in combination with the substantially air tight connection.

An auger 13 is disposed in the throat 19 of the hopper 11. In an example, the auger can be a vertically oriented auger, in another example the auger can be a horizontally oriented auger, and in yet another example oriented at a position intermediate the horizontal and vertical. In another example, the auger can at least partially sit inside the hopper. The auger can act as a meter that can control the feed rate of powder flow into disperser 12. If the powder flows too quickly into the disperser then agglomerates can form, which can cause plugged lines and filters and additional waste.

Additional information on the hopper including the auger can be found in U.S. Pat. No. 6,712,496, incorporated by reference herein.

In an example, each solid powder can be fed through the same hopper. In another example, the suspension system components can be fed through more than one hopper.

The suspension system components go from hopper 11 and then into disperser 12 at a controlled rate. In disperser 12 the suspension system components, which can be a solid powder, are combined with an aqueous media. The aqueous media is from main mix tank 14 and travels from main mix tank 14 through in-feed pump 15 (commercially available as Universal I Series Pump, SPX, Delavan, Wis., USA) to disperser 12. For the first solid powder that is added, which can be MAS in some examples, the aqueous media can be water. For the subsequent suspension system components and other ingredients that are added, the aqueous media can be the contents of main mix tank 14. After being combined with the fluid at the disperser the aqueous media can go through discharge pump 16 (commercially available as Universal I Series positive displacement pump, Waukesha Cherry-Burrell®, Delavan, Wis., USA) and goes to main mix tank 14.

The bismuth slurry, dye, and liquid minors can be fed through in-feed pump 15, to disperser 12 where they are combined with the liquid contents of the main mix storage, and then go through discharge pump 16 and then to main mix tank 14. In another example these pre-mixes can be added directly to the tank. The liquid minors can include water, a sweetener such as sucralose, preservatives such as sorbic acid and benzoic acid, flavorings including methyl salicylate, and buffers such as salicylic acid.

In one example, the contents can be added in the following order: MAS, gellan gum, dye premix, bismuth slurry, methyl cellulose, and then the liquid minors premix. Additional water can be added after the dye premix and after the bismuth slurry to clean the process of the present invention and help ensure that the material has been incorporated into the formulation and after the liquid minors to make sure that the specified weight has been made. In some examples, adding the components in this order can create a liquid suspension with desired rheology. In one example, the gellan gum is added after the MAS and/or methyl cellulose and/or bismuth slurry. In another example, the gellan gum is added before the MAS and/or methyl cellulose and/or bismuth slurry. In another example the bismuth slurry is added before the gellan gum and/or MAS and/or methyl cellulose. In another example the bismuth slurry is added after the gellan gum and/or methyl cellulose and/or MAS.

After all the materials have been added, the formulation goes from main mix tank 14 and optionally to filter 17, and then into storage tank 18. In one example, the filter can be a 177 micron mesh. The filter can remove undesired larger particulates, including agglomerates, that might be in the formulation. In an example, the formulation can pass through another filter before bottling. In another example, the formulation does not pass through a filter.

In another example, the disperser can be replaced or eliminated. For instance, in an example, the suspension system components are added directly to the main mix tank.

In another example, the suspension system components can be metered and incorporated into the formulation without incorporating additional air into the process. In another example, a centrifugal pump (commercially available as a Tri-Blender® from Oliver M. Dean, Inc., Worchester, Mass.) that can pull powder from the hopper can be used. In another example, a mill or shear mixer (commercially available from IKA®, Wilmington, N.C., USA) can be used. In another example, a solid state eductor (Fox Valve, Dover, N.J., USA) can be used. In another example, a Quadro ZC disperser (commercially available from Quadro Engineering, Waterloo, Ontario, Canada).

In another example, the impeller in main mix tank 14, in-feed pump 15 (commercially available as Universal I Series Pump, SPX, Delavan, Wis., USA), disperser 12, and discharge pump 16 (commercially available as Universal I Series Pump, SPX, Delavan, Wis.) adds shear force to the formulation to ensure adequate mixing.

In an example, the in-feed pump and/or the discharge pump can be a positive displacement pump. In another example, the in-feed pump and/or the discharge pump can be a centrifugal pump. In yet another example, a centrifugal pump can be used as the in-feed pump and/or the discharge pump.

In another example, the initial low shear viscosity (LSV) of the formulation at 25° C. at a shear rate of 0.1/s ($s^{-1}$), as measured by the Rheology Test Method described herein, is greater than about 1500 centiPoise (cP), in another example greater than 1700 cP, in another example greater than about 1800 cP, in another example greater than about 1900 cP, in another example greater than about 2000 cP, in another example greater than about 2100 cP, in another example greater than about 2200 cP, and in another example greater than about 2300 cP.

Examples of some of the components that can be used to make suspensions according to the methods of the present invention are listed below.

Internal Phase

The methods of the present invention can be used to suspend any internal phase, including actives, in a suspension.

In an example, the pharmaceutical active, such as a bismuth-containing pharmaceutical agent, which can be in the form of a pharmaceutically-acceptable salt. Non-limiting examples of bismuth-containing pharmaceutical agents can include bismuth aluminate, bismuth subcarbonate, bismuth subcitrate, bismuth citrate, tripotassium dicitrato bismuthate, bismuth subgallate, bismuth subnitrate, bismuth tartrate, bismuth subsalicylate, and mixtures thereof. In an example, the pharmaceutical formulation can contain bismuth subsalicylate (BSS).

The liquid formulations of the present invention can contain from about 0.1% to about 10% of a bismuth-containing pharmaceutical agent, in another example from about 0.5% to about 5%, in another example from about 1% to about 4%, and in another example from about 1.5% to about 2.5%. In another example the formulation can contain from about 0.2% to about 8% of a bismuth-containing pharmaceutical agent, in another example from about 1% to about 6%, and in another example from about 2% to about 4%.

In another example the internal phase can be silica. In another example, the internal phase can be titanium dioxide. In another example, the internal phase can be zinc oxide. In another example, the internal phase can be zinc pyrithione.

Suspension System

The formulations can contain a suspension system capable of suspending the active, which can include a bismuth-containing pharmaceutical agent, and the other components in an aqueous media. In an example, the suspension system can be added to the formulation as a powder.

In an example, the suspension system can have a suspension system component with a high molecular weight. In an example, the molecular weight of the suspending agent is greater than about 500,000 Daltons, in another example greater than about 1 million Daltons, in another example greater than about 1.5 million Daltons, and in another example greater than about 2 million Daltons.

In another example, the suspension system can have a suspending agent that is charged. In an example, the suspension agent can have an anionic charge and in another example the suspension agent can have a cationic charge.

In an example, a suspending agent can be gellan gum. In an example the liquid formulation can contain from about 0.001% to about 0.1% gellan gum, in another example from about 0.005% to about 0.06%, in another example from about 0.01% to about 0.05%, and in another example 0.02% to about 0.04%.

In an example, the suspension system can contain magnesium aluminum silicate, with the chemical formula $Al_2MgO_8Si_2$, which occurs naturally in such smectite minerals as colerainite, saponite, sapphirine, and montmorillonite. In an example, the formulation can contain from about 0.001% to about 2% magnesium aluminum silicate, in another example from about 0.01% to about 0.5%, in another example from about 0.05% to about 0.2%, and in another example from about 0.075% to about 0.125%. In an example the formulation contains about 0.3% or less magnesium aluminum silicate, in another example about 0.25% or less, in another example about 0.2% or less, in another example 0.15% or less, in another example 0.10% or less, in another example 0.05% or less. In an example, the formulation is free of magnesium aluminum silicate.

In another example, the suspension system can comprise a non-ionic cellulose ether polymer. Non-limiting examples of non-ionic cellulose ether polymers can be selected from the group consisting of alkylcelluloses (e.g., methyl cellulose), hydroxyalkylalkylcelluloses (e.g., hydroxypropylmethyl cellulose: hydroxybutylmethyl cellulose; hydroxyethylmethyl cellulose; ethylhydroxyethylcellulose), hydroxyalkylcelluloses (e.g., hydroxyethylcellulose; hydroxypropylcellulose), carboxymethyl cellulose sodium, microcrystalline cellulose, a combination of carboxymethyl cellulose sodium and microcrystalline cellulose (e.g. Avicel RC-591 of FMC Corp.), and mixtures thereof. In an example, the formulation can contain alkylcelluloses. In an example, the formulation can contain methyl cellulose. In an example, the formulation can contain from about 0.1% to about 5% non-ionic cellulose ethyl polymer, in another example from about 0.1% to about 3%, in another example from about 0.5% to about 1.5%, and in another example from about 0.75% to about 1.3%.

In another example, the suspension system can include a component selected from the group consisting of carboxymethyl cellulose sodium, microcrystalline cellulose, a combination of carboxymethyl cellulose sodium and microcrystalline cellulose, xanthan gum, silicon dioxide, and mixtures thereof.

In another example, the suspension system can include a synthetic clay such as a collaoidal layered silicate (Laponite) clay (BYK, Wesel, Germany). Non-limiting examples of laponite clays can include lithium magnesium silicate, lithium magnesium sodium silicate, and combinations thereof.

In another example, the suspension system can include bentonite, which are absorbent aluminum phyllosilicates.

In another example the suspension system can include clay minerals selected from the kaolin group which can include the minerals kaolinite, dickite, halloysite, and/or nacrite; the smectite group which can include dioctahedral smectites such as montmorillonite, nontronite, and/or trioctahedral smectites; the illite group which can include clay-micas; the chlorite group; attapulgite clays; sepiolite; and combinations thereof.

Buffers

In an example the liquid medication can contain from about 0.001% to about 1% buffer, in another example from about 0.01% to about 0.5% buffer, in another example from about 0.02% to about 0.3% buffer, and in another example from about 0.05% to about 0.15% buffer. Non-limiting examples of buffers can include acetic acid, sodium acetate, citric acid, sodium citrate, monobasic sodium phosphate, dibasic sodium phosphate, sodium carbonate, sodium bicarbonate, succinic acid, sodium succinate, potassium dihydrogen phosphate, phosphoric acid, salicylic acid, and combinations thereof.

Preservative

The formulation can contain a preservative. Non-limiting examples of preservatives can include benzalkonium chloride, ethylenediaminetetraacetic acid (EDTA), benzyl alcohol, potassium sorbate, parabens, benzoic acid, sorbic acid, sodium benzoate, and mixtures thereof. The formulation can contain from about 0.01% to about 0.5% preservative, in another example from about 0.02% to about 0.1%, and in another example from about 0.03% to about 0.05%.

Water

The liquid formulations can further comprise from about 80% to about 99% water, in another example from about 90% to about 99%, and in another example from about 93% to about 98%.

Optional Components

The formulations can contain additional optional components selected as appropriate for the particular formulation being prepared.

Some examples of substances that can serve as optional components can include sugars such as lactose, glucose and sucrose; non-nutritive sweeteners such as saccharin, aspartame, acesulfame, sucralose, and cyclamate; coloring agents; flavoring agents such as methyl salicylate, peppermint oil, and cherry flavor; etc. In an example, the sweetener is sucralose. In another example, the sweetener can contain sodium saccharin.

Other compatible pharmaceutical additives and actives (e.g., non-steroidal anti-inflammatory drugs such as aspirin, ibuprofen, and naproxen; acetaminophen; $H_2$ receptor antagonists; antacids) may be included in the pharmaceutically-acceptable optional components for use in the formulations of the present invention.

Density Test Method

In order to calculate the density of the formulation, the following procedure can be used. A DMA 46 Digital Density Meter (available from Mettler Instrument Corp., Princeton, N.J. USA) and a disposable LuerLok™ syringe (available from Fisher Scientific, Hampton, N.H., USA) are used.

Slowly fill the syringe to get a sample that is approximately 20 mL. There should be little to no air left in the syringe. Make sure the sample is homogeneous and free of visible air bubbles in order to get accurate results. If the sample is not free of bubbles, get another sample or expel a portion of the sample to remove the visible air bubbles. Then, allow for at least ten minutes for the sample temperature to equilibrate.

If needed, perform the day-of-use check as required for the instrument according to the instructions provided by the manufacturer.

Inject the sample to be measured into the oscillator cell in the same manner as for water, inject the sample very slowly about 0.5-1 mL per second to avoid shattering the fragile glass cell. Temperature equilibrium is reached when the displayed value remains the same within one digit in the fourth place. Record the result from the display.

Mean Length Test Method

In order to calculate the average diameter size of the particles and aggregates herein, including the gellan gum aggregates, the following procedure can be used. A Horiba LA-910 (available from Horiba Scientific) can be used with LA-910 Display Module Version 1.04 software.

First, the LA-910 is turned on and allowed to warm-up for 30 minutes. Then, the circulation tubing is inspected for any cracks and wear and replaced if necessary. The LED laser alignment arrows on the side of the instrument are also checked and if less than three of the arrows are lit, a manual adjustment for laser light alignment is performed according to the instructions in the instrument manual.

The computer is turned on and the software is opened and minimized. The liquid measure program is opened and the relative refractive index (RRI) for the sample being tested is set. The index of many refractive indexes (RI) is found in the instrument manual. For those materials not listed, check in another chemical reference book or call Horiba Technical Services for help. The RRI is calculated with the following equation:

$$RRI = \frac{RI \text{ of Particle}}{RI \text{ of Dispersant}}$$

After the warm-up period, circulate DI water through the system to purge any remaining particles or dirt from the system. Then, fill the sample cup to approximately 0.5 inches (1.27 cm) below the drain hole with carrier liquid. Water will be the carrier liquid for most samples, but methanol or other solvents may be used when appropriate.

When the channel markers are or near the bottom of the channels and there is no visible interference, "blank" the carrier liquid. Begin agitation and circulation at desired speed for the sample type. The ultrasonic feature may be turned on at this point if needed.

Use a well-mixed, representative sample, but do not mix or shake excessively, causing air bubbles. Start the agitation and circulation. Carefully dropper the sample to be measured into the carrier liquid, monitoring the He—Ne laser (purple line) and tungsten lamp (blue line) indicators. When the indicator lines are within the green area, indicating a sufficient particle population for measurement, click on the "measure" icon and report the mean particle size.

Rheology Test Method

In order to measure and calculate the rheology, in including LSV and the initial LSV, the following procedure can be used. TA Instrument AR 2000 Rheometer (available from TA Instruments, New Castle, Del.) with a Couette setup (cup and bob), Stainless Steel Standard DIN or concentric cylinder. The inner radius is 15.18 mm, the rotor outer radius is 14.01 mm, the cylinder immersed height is 42.02 mm, and the gap is 5920 µm.

The test is run at 25° C. with a 23 mL sample. The procedure is run with a stepped flow from 0.0100 s$^{-1}$ shear rate to 100.0 s$^{-1}$ shear rate at 10 points/decade.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

All parts, percentages and proportions referred to herein and in the claims are by weight of the total formulation unless otherwise indicated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a liquid pharmaceutical suspension comprising:
   a. mixing magnesium aluminum silicate with an aqueous media to form a first mixture;
   b. mixing gellan gum with the first mixture to form a second mixture;
   c. mixing a bismuth slurry with the second mixture to form a third mixture; and
   d. mixing methyl cellulose with the third mixture to form a liquid suspension.

2. The method of claim 1 comprising from about 0.005% to about 0.1% gellan gum.

3. The method of claim 2 comprising from about 0.01% to about 0.05% gellan gum.

4. The method of claim 2 comprising from about 0.01% to about 0.5% magnesium aluminum silicate.

5. The method of claim 4 comprising from about 0.1% to about 5% methyl cellulose.

6. The method of claim 1 wherein the bismuth slurry comprises from about 5% to about 40% bismuth subsalicylate.

7. The method of claim 1 further comprising adding a buffer to the liquid suspension.

8. The method of claim 1 wherein the method is performed at ambient temperature.

9. A method of making a suspension comprising:
   a. adding a suspension system component to an aqueous media to form a first mixture utilizing a hopper for containing the suspension system component, the hopper having a hopper inlet for receiving the suspension system component and a throat for distributing the suspension system component; the throat comprises a throat inlet for receiving solids from the hopper and a throat outlet for discharging solids from the throat wherein a vertically oriented auger is disposed in the throat wherein the throat outlet is connected to a disperser at a connection and wherein the connection is substantially free of air; and
   b. adding an internal phase to form a suspension;
   wherein the suspension system component comprises gellan gum and wherein the gellan gum is a powder.

10. The method of claim 9 wherein the internal phase comprises a bismuth slurry comprising from about 7% to about 30% bismuth subsalicylate.

11. The method of claim 9 comprising from about 0.01% to about 0.06% gellan gum.

12. The method of claim 9 wherein the suspension system component comprises magnesium aluminum silicate and wherein the magnesium aluminum silicate is a powder.

13. The method of claim 12 comprising from about 0.02% to about 0.04% gellan gum.

14. The method of claim 9 wherein the suspension system component comprises methyl cellulose and wherein the methyl cellulose is a powder.

15. A method of producing a suspension comprising:
   a. adding gellan gum to an ionic solution at ambient temperature to form a first mixture; and
   b. adding a bismuth slurry comprising from about 7% to about 30% bismuth subsalicylate to the first mixture to form a liquid suspension.

16. The method of claim 15 comprising from about 0.01% to about 0.5% magnesium aluminum silicate.

17. The method of claim 15 comprising from about 0.01% to about 0.06% gellan gum.

18. The method of claim 15 further comprising adding methyl cellulose.

19. The method of claim 18 comprising adding from about 0.1% to about 5% methyl cellulose.

20. The method of claim 5 wherein the bismuth slurry comprises bismuth subsalicylate particles with an average diameter from about 1 µm to about 25 µm.

* * * * *